United States Patent
Tokita

(10) Patent No.: US 9,883,806 B2
(45) Date of Patent: Feb. 6, 2018

(54) LIGHT IRRADIATING APPARATUS, CONTROL METHOD THEREFOR, AND OBJECT INFORMATION ACQUIRING APPARATUS

(75) Inventor: Toshinobu Tokita, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 67 days.

(21) Appl. No.: 14/113,679

(22) PCT Filed: Apr. 25, 2012

(86) PCT No.: PCT/JP2012/061632
§ 371 (c)(1),
(2), (4) Date: Oct. 24, 2013

(87) PCT Pub. No.: WO2012/150721
PCT Pub. Date: Nov. 8, 2012

(65) Prior Publication Data
US 2014/0051971 A1    Feb. 20, 2014

(30) Foreign Application Priority Data
May 2, 2011 (JP) .................. 2011-102841

(51) Int. Cl.
*A61B 5/05*   (2006.01)
*A61B 5/00*   (2006.01)

(52) U.S. Cl.
CPC .......... *A61B 5/0095* (2013.01); *A61B 5/6843* (2013.01)

(58) Field of Classification Search
CPC ... A61B 5/0095; A61B 5/6843; G06F 3/0414; G06F 3/044; G06F 3/042; H03K 17/962
See application file for complete search history.

(56) References Cited

U.S. PATENT DOCUMENTS

2004/0176754 A1* 9/2004 Island ............ A61B 18/203 606/9
2006/0176754 A1   8/2006 Chen ................. 365/230.03
(Continued)

FOREIGN PATENT DOCUMENTS

JP   A 2005-278724    10/2005
JP   A 2006-525036    11/2006
(Continued)

OTHER PUBLICATIONS

S.A. Ermilov et al., "Development of Laser Optoacoustic and Ultraosonic Imaging System for Breast Cancer Utilizing Handheld Array Probes", *Photons Plus Ultrasound: Imaging and Sensing 2009* (Proc of SPIE, vol. 7177, 717703-1 (2009).

Primary Examiner — Ellsworth Weatherby
(74) Attorney, Agent, or Firm — Fitzpatrick, Cella, Harper & Scinto

(57) ABSTRACT

A light irradiating apparatus is used, which is characterized by having: a probe including an irradiating unit which guides light to an object, a housing containing the irradiating unit, and a touch sensor acquiring a contact condition amount between the object and the housing; and a controller controlling irradiation with light from the irradiating unit based on a level of the contact condition amount and a change in the contact condition amount, wherein in a case where the contact condition amount is equal to or more than a first reference value while the change in the contact condition amount which occurs when the housing is pressed against the object is a positive value, the controller performs a control which enables irradiation with light from the irradiating unit when the change in the contact condition amount is equal to or more than a second reference value.

6 Claims, 7 Drawing Sheets

(56) References Cited

U.S. PATENT DOCUMENTS

| | | | |
|---|---|---|---|
| 2007/0015978 A1* | 1/2007 | Kanayama | A61B 5/0095 600/310 |
| 2007/0181139 A1 | 8/2007 | Hauck | 128/899 |
| 2008/0232604 A1 | 9/2008 | Dufresne et al. | 381/67 |
| 2009/0163787 A1* | 6/2009 | Mannheimer | A61B 5/14552 600/324 |
| 2010/0252408 A1* | 10/2010 | Yamauchi | H03K 17/962 200/600 |
| 2011/0230762 A1 | 9/2011 | Tokita et al. | 600/437 |
| 2011/0245667 A1 | 10/2011 | Tokita | 600/437 |
| 2012/0150012 A1 | 6/2012 | Fujimoto et al. | 600/407 |
| 2012/0238859 A1 | 9/2012 | Tokita et al. | 600/407 |
| 2012/0302865 A1 | 11/2012 | Tokita et al. | 600/407 |
| 2013/0061678 A1 | 3/2013 | Yamamoto et al. | 73/62 |
| 2013/0167648 A1 | 7/2013 | Tokita | 73/655 |
| 2014/0046166 A1 | 2/2014 | Tokita | 600/407 |
| 2014/0051971 A1 | 2/2014 | Tokita | 600/407 |

FOREIGN PATENT DOCUMENTS

| | | | |
|---|---|---|---|
| JP | A 2008-289809 | 12/2008 | |
| JP | A 2012-231978 | 11/2012 | |
| WO | WO 2004/042382 | 4/2004 | |
| WO | WO 2004/080279 | 9/2004 | |
| WO | WO 2008082184 A1 * | 7/2008 | G06F 3/044 |

\* cited by examiner

LIGHT IRRADIATING APPARATUS, CONTROL METHOD THEREFOR, AND OBJECT INFORMATION ACQUIRING APPARATUS

CROSS-REFERENCE TO RELATED APPLICATION

This application claims the benefit of Japanese Patent Application No. 2011-102841, filed on May 2, 2011, which is hereby incorporated by reference herein in its entirety.

TECHNICAL FIELD

The present invention relates to a light irradiating apparatus, a control method therefor, and an object information acquiring apparatus.

BACKGROUND ART

Attention has been focused on photoacoustic tomography (hereinafter will be referred to as "PAT") as a method of specifically imaging neovascularization which occurs due to cancer. PAT is a method including illuminating an object with illuminating light (near infrared rays) and receiving a photoacoustic wave generated from the inside of the object by means of an ultrasound probe, thereby imaging the photoacoustic wave.

Non Patent Literature 1 describes a handheld type photoacoustic apparatus. This apparatus has a bundle fiber, which is fixed to a handheld type probe, for irradiation with light from a light source. Non Patent Literature 1, however, is silent on a contact between an illuminating light emitting surface and an object. Therefore, the illuminating light is emitted not only to the object but also into other space and, hence, there is room to improve the safety against the illuminating light.

This problem can be addressed by using the technique described in Patent Literature 1. FIGS. 7A and 7B illustrate a system configuration shown in Patent Literature 1. In FIG. 7, an energy emitting surface 101 is a surface for contact with skin from which energy, such as light, is emitted. A support structure 102 fixes the energy emitting surface 101 and is housed in a housing 104 with contact sensors 103 intervening therebetween. The contact sensors 103 are each configured to detect a contact between the energy emitting surface 101 and non-illustrated skin and are disposed to circumscribe the energy emitting surface 101. Energy emission is stopped unless the contact between the contact sensors 103 and the skin is detected. By so doing, energy irradiation is conducted only when the energy emitting surface 101 is completely in intimate contact with the skin, which leads to improved safety against energy irradiation.

CITATION LIST

Patent Literature

PTL 1: Japanese Translation of PCT Application No. 2006-525036

Non Patent Literature

NPL 1: S. A. Ermilov et al., Development of laser optoacoustic and ultrasonic imaging system for breast cancer utilizing handheld array probes, Photons Plus Ultrasound: Imaging and Sensing 2009, Proc. of SPIE vol. 7177, 2009.

SUMMARY OF INVENTION

Technical Problem

The conventional art, however, involves the following problems.

Since Non Patent Literature 1 is silent on the contact between an illuminating light emitting surface and the object, the illuminating light is undesirably emitted into a space other than object. Even when the operator tries to bring the energy emitting surface into intimate contact with skin carefully, it is possible that the energy emitting surface and the skin fail to be brought into intimate contact with each other completely and that, when the energy emitting surface is only partially brought into contact with the skin, the energy emitting surface leans against the skin on one side to define a clearance therebetween. For this reason, there is room to improve the safety against the illuminating light.

The problem can be relieved by using the technique described in Patent Literature 1. Specifically, the contact sensors for contact with skin are disposed around the illuminating light emitting surface to perform a control for stopping emission of the illuminating light unless the contact sensors detect the contact. In order to prevent the energy emitting surface from leaning against the skin on one side, however, a multi-stage emission preventing mechanism, such as the provision of a multiplicity of contact sensors around the illuminating light emitting surface, is needed, which results in a complicated system configuration.

The present invention has been made with the foregoing problems in view. An object of the present invention is to simplify the system configuration of an apparatus having a mechanism for irradiating the object with light, as well as to secure the safety against the illuminating light.

Solution to Problem

The present invention provides a light irradiating apparatus comprising:

a probe including an irradiating unit which guides light from a light source to an object, a housing containing the irradiating unit, and a touch sensor acquiring a contact condition amount between the object and the housing; and a controller controlling irradiation with light from the irradiating unit based on a level of the contact condition amount and a change in the contact condition amount, wherein in a case where the contact condition amount is equal to or more than a first reference value while the change in the contact condition amount which occurs when the housing is pressed against the object is a positive value, the controller performs a control which enables irradiation with light from the irradiating unit when the change in the contact condition amount is equal to or more than a second reference value.

The present invention also provides a method for controlling a light irradiating apparatus having: a probe including an irradiating unit which guides light from a light source to an object, a housing containing the irradiating unit, and a touch sensor acquiring a contact condition amount between the object and the housing; and a controller controlling irradiation with light from the irradiating unit, the method comprising:

a step of causing the controller to determine whether or not a change in the contact condition amount is equal to or more than a second reference value in a case where the contact condition amount is equal to or more than a first reference value while the change in the contact condition amount which occurs when the housing is pressed against the object is a positive value; and a step of causing the controller to perform a control which enables irradiation with light from the irradiating unit in a case where the contact condition amount is equal to or more than the first reference value while the change in the contact condition amount is determined to be equal to or more than the second reference value.

Advantageous Effects of Invention

According to the present invention, the system configuration of an apparatus having a mechanism for irradiating the object with light can be simplified while securing the safety against the illuminating light.

Further features of the present invention will become apparent from the following description of exemplary embodiments with reference to the attached drawings.

DESCRIPTION OF EMBODIMENTS

Hereinafter, preferred embodiments of the present invention will be described with reference to the drawings. The present invention is applicable to apparatuses utilizing a photoacoustic effect for acquiring object information as image information by receiving an acoustic wave that is generated in an object by irradiating the object with light (electromagnetic wave). (Such an acoustic wave is also called a "photoacoustic wave", a typical example of which is an ultrasound wave.) Such apparatuses are called "photoacoustic apparatuses".

The object information to be acquired means a distribution of generation sources of acoustic waves generated by irradiation with light, an initial sound pressure distribution inside the object, an absorbed optical energy density distribution or absorption coefficient distribution derived from the initial sound pressure distribution, or a concentration distribution of a substance forming a tissue. The concentration distribution of a substance is meant to include, for example, an oxygen saturation distribution and an oxidized-reduced hemoglobin concentration distribution.

The "acoustic wave" is typically an ultrasound wave and is meant to include elastic waves such as called a sound wave, an ultrasound wave, an acoustic wave, a photoacoustic wave, and a photoultrasound wave. The "light", as used in the present invention, is meant by electromagnetic waves including visible rays and infrared rays. Light of a specific wavelength is simply selected to meet a component to be measured by the object information acquiring apparatus.

The following description is directed to the object, though the object does not form part of the object information acquiring apparatus of the present invention. The object information acquiring apparatus according to the present invention is capable of diagnosing malignant tumors, vascular diseases, blood sugar levels and the like of humans or animals, making follow-up of chemotherapy, and the like. Therefore, the object is assumed as a living body, specifically, a breast, finger, limb or the like of a human or animal. A light absorbing substance present inside the object is a substance having a relatively high absorption coefficient among substances present inside the object. For example, in cases where a human body is a subject of measurement, such light absorbing substances include oxidized or reduced hemoglobin and a blood vessel containing such hemoglobin, and a malignant tumor containing a number of neovascular vessels. When the object is a living body, the apparatus of the present invention can be called a "living body information processing apparatus".

Figure 1:
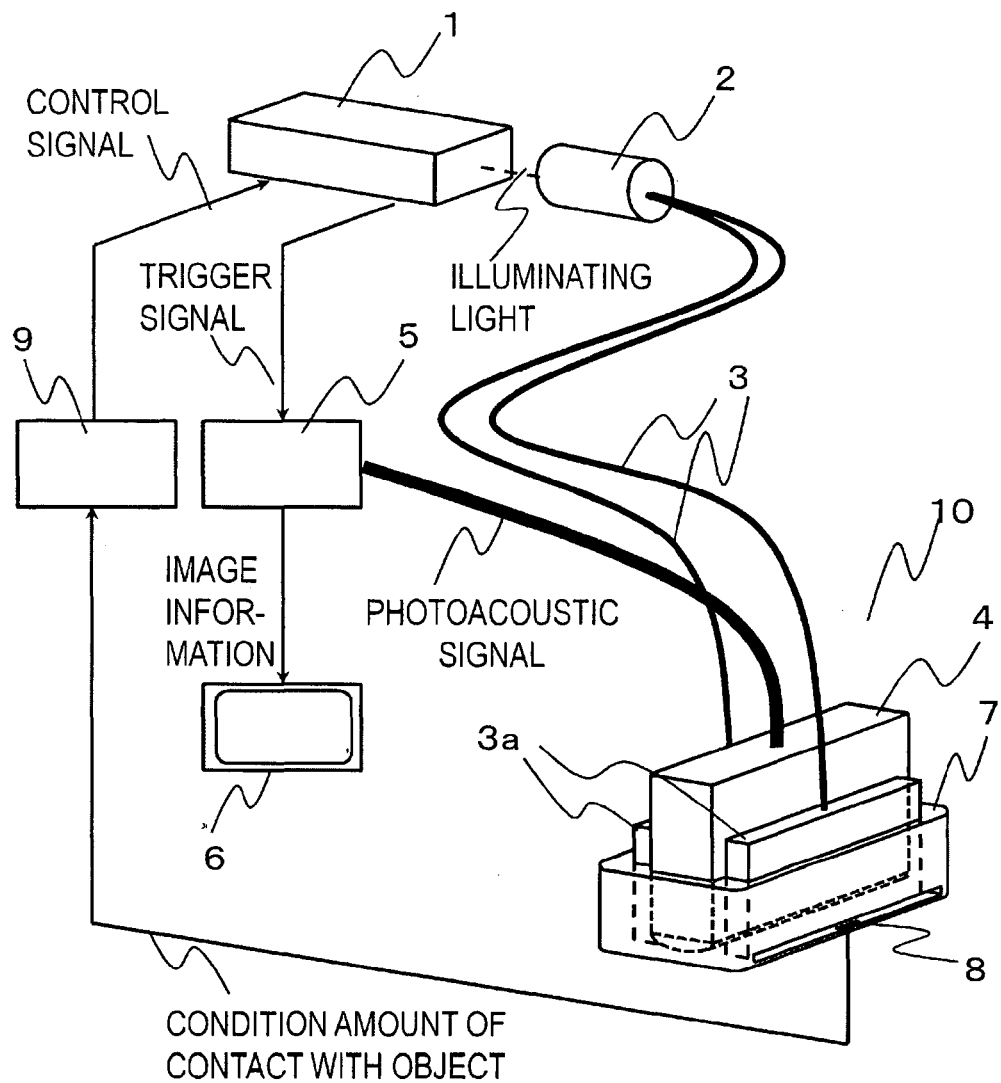
FIG. 1 is a view illustrating a system configuration according to an embodiment of the present invention.

Description will be made of an embodiment with reference to FIG. 1. FIG. 1 schematically illustrates a handheld type photoacoustic apparatus.

A light source 1, an illuminating optical system 2 and a bundle fiber 3 are constituent elements for illuminating a non-illustrated object with near infrared rays. A pulse laser, such as an Nd:YAG laser or an alexandrite laser, is used as the light source 1. Alternatively, use may be made of a Ti:Sa laser or OPO laser which uses Nd:YAG laser light as excitation light. Yet alternatively, a light source other than such lasers, such as a xenon lamp, may be used. The illuminating optical system 2 expands illuminating light from the light source 1 and causes the illuminating light to become incident on the bundle fiber 3. The illuminating light passes through the bundle fiber 3 to illuminate the object. Though the bundle fiber shown in FIG. 1 is branched into two, the number of branches is any desired number. Though FIG. 1 does not show an illuminating optical system for guiding the illuminating light from the bundle fiber 3 to the object, it is possible to illuminate the object directly from an irradiating end 3a of the bundle fiber 3 or to provide any desired optical system such as a diffuser. The irradiating end 3a is equivalent to the "irradiating unit" defined by the present invention.

An ultrasound probe 4 is configured to receive a photoacoustic wave generated from the object. A one- or two-dimensional array of detecting elements such as PZTs or CMUTs, for example, can be used as the ultrasound probe 2. Alternatively, an ultrasound probe formed of a single element may be used. A processing device 5 acquires a photoacoustic signal received by the ultrasound probe 4 at the timing of input of a trigger signal for causing emission of illuminating light. The processing device 5 performs amplification, digital conversion, detection and like processing of the photoacoustic signal to create image information and causes a monitor 6 to display the image information.

A housing 7 is configured to be fitted with the ultrasound probe 4 and the irradiating end 3a of the bundle fiber. The housing 7 is provided with a touch sensor 8. The touch sensor 8 is a sensor configured to measure the contact condition amount between the object and the housing 7. The output of the touch sensor 8 is inputted to a controller 9. The controller 9 generates a light emission control signal from the output of the touch sensor 8 and transmits the signal to the light source 1. A handheld probe 10 comprises the light irradiating end 3a of the bundle fiber, ultrasound probe 4, housing 7, and touch sensor 8. Whether irradiation of the object with light is permitted or has to be stopped depends on the signal from the controller.

The processing device 5 and the controller 9 can be implemented by using an information processor for example. The information processor may perform different processing operations by using respective circuits dedicated thereto or may be implemented in the form of a program for operating a computer having a CPU or the like.

Figure 2:
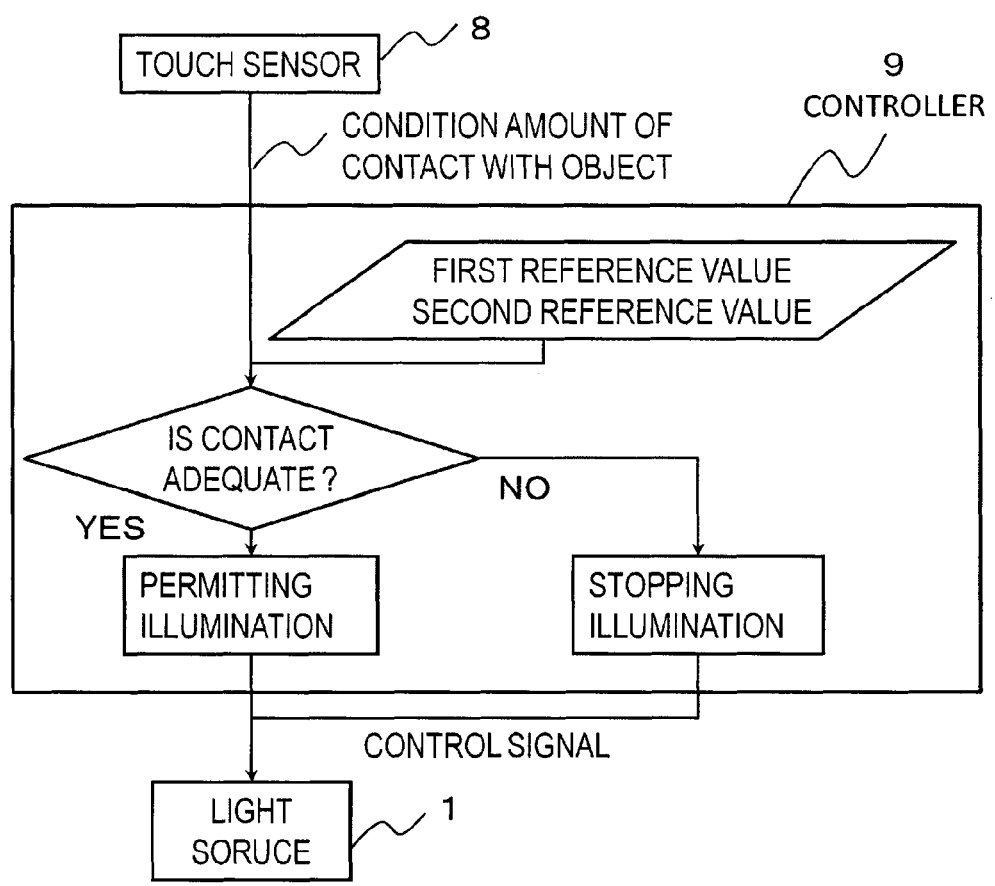
FIG. 2 is a diagram illustrating a controller according to the embodiment of the present invention.

With reference to FIG. 2, description is made below of a control method carried out by the controller 9.

As shown in FIG. 2, the condition amount of contact with the object outputted from the touch sensor 8 is inputted to the controller 9. The controller 9 determines a contact condition from the contact condition amount and permits illumination when the contact is adequate. When the contact is inadequate, the controller 9 stops illumination. The control signal is transmitted to the light source 1 and is used for light emission control.

A method for determination of the contact condition is carried out by comparing the contact condition amount indicative of the degree of contact to a first reference value and comparing the degree of change in the contact condition amount (e.g., temporal differential) to a second reference value. The condition for permitting illumination is that the contact condition amount is equal to or more than the first reference value while the change in contact condition is equal to or more than the second reference value. With respect to the change in contact condition, a change that occurs in pressing the housing against the object is expressed as a positive value, while a change that occurs in separating the housing from the object is expressed as a negative value. A certain negative value serves as the second reference value. For example, illumination is permitted on condition that the temporal differential of a condition amount measured by the touch sensor 8 is equal to or more than the second reference value.

When the contact condition amount indicative of the degree of contact is equal to or more than the first reference value, the housing 7 is determined as being in adequate contact with the object without leaning against the object on one side. When the temporal differential of the contact condition amount is equal to or less than the second reference value, the handheld probe 10 is determined as being about to separate from the object. That is, the handheld probe 10 can be determined as assuming not only a condition in which the handheld probe 10 is about to completely separate from the object but also a condition in which the handheld probe 10 is about to lean against the object on one side. For this reason, even when sensors for detection of contact are disposed in such a manner as not to circumscribe the illuminating area, the illumination control signal can be quickly transmitted to the light source 1 before the handheld probe 10 is separated from the object. Therefore, the safety against laser irradiation can be secured without the need to provide a multiplicity of sensors.

The present invention is characterized by an illuminating light emission control based on the condition of contact with the object. Therefore, constituent elements provided on the optical path are not limited to the illuminating optical system 2 and the bundle fiber 3. For example, instead of the bundle fiber 3, a mirror, a prism and a light-shielding tube accommodating these components therein are provided to secure the optical path extending up to a position for illuminating the object.

Either a method including opening and closing an internal shutter of the light source 1 or a method including controlling an internal trigger signal is effective for the light emission control over the light source 1. While the control signal from the controller 9 has been described as a signal for the light emission control over the light source 1, there is no limitation to this feature. For example, it is possible that an external shutter is provided between the light source 1 and the illuminating optical system 2 while the opening and closing of the shutter is controlled by such a control signal.

The following description is directed to the touch sensor 8. The touch sensor 8 used in the present invention may be a sensor of any type that is capable of measuring the contact condition amount between the housing 7 and the object. For example, use can be made of any type of sensor that can measure the condition amount, such as force, pressure and distance, based on a principle utilizing optics, resistance, electrostatic capacitance or the like. Here, an arrangement using a strain gauge as the touch sensor 8 is described.

Figure 3A:
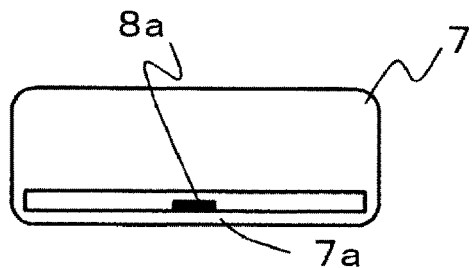
FIGS. 3A to 3D are views illustrating the mounting of a touch sensor according to the embodiment of the present invention.
Figure 3B:
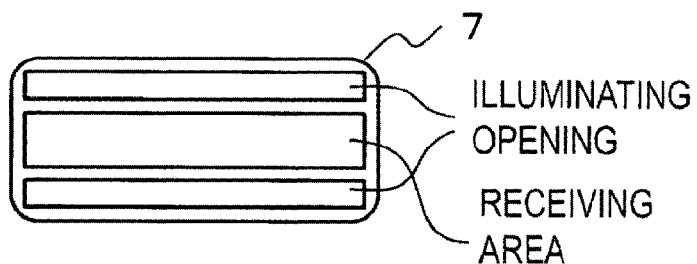
Figure 3C:
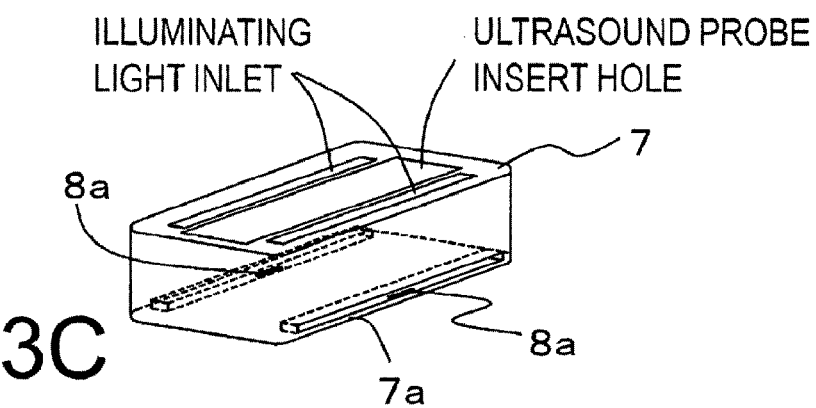

FIG. 3A is a side elevational view of the housing 7, FIG. 3B is a bottom view of the housing 7, and FIG. 3C is a perspective view of the housing 7. As shown in the bottom view of FIG. 3B, the bottom surface of the housing 7 is divided into an opening area for illuminating the object and a photoacoustic wave receiving area. In mounting a strain gauge 8a on the housing 7, the strain gauge 8a is bonded to a flat spring 7a forming part of the housing 7. By so doing, the strain gauge 8a produces an output with increased sensitivity to the condition of contact with the object. For this reason, the contact condition amount (i.e., strain of the flat spring 7a) can be measured highly precisely. Therefore, the stability of the control by the controller 9 is improved and, hence, the safety against light irradiation can be secured even when the number of touch sensors 8 is reduced by disposing touch sensors 8 in such a manner as not to circumscribe the illuminating opening. Further, the improved stability of the control by the controller 9 leads to reduced occurrence of errors such as illuminating in non-contact condition and failing to illuminate in a contact condition, thereby making it possible to use the photoacoustic apparatus stably.

Figure 3D:
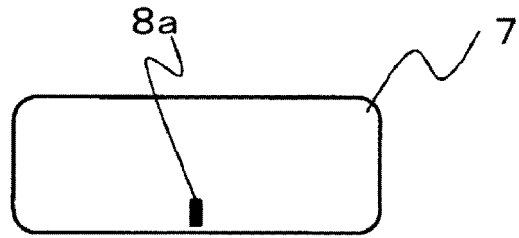

The position of the strain gauge 8a is not limited the position at which the strain gauge 8a is bonded to the flat spring 7a. As shown in the side elevational view of FIG. 3D, it is possible that the housing 7 is formed from a material which is easy to strain while the strain gauge 8a is bonded to a side surface of the housing 7.

Alternatively, touch sensors 8 (strain gauges 8a), the number of which is two or so, may be disposed across the illuminating opening (illuminating optical path) as shown in FIG. 3C. With this arrangement, the light emission control based on the contact condition amount and the change in the contact condition amount makes it possible to secure the safety as well as to simplify the system configuration.

Embodiment 1

Figure 4A:
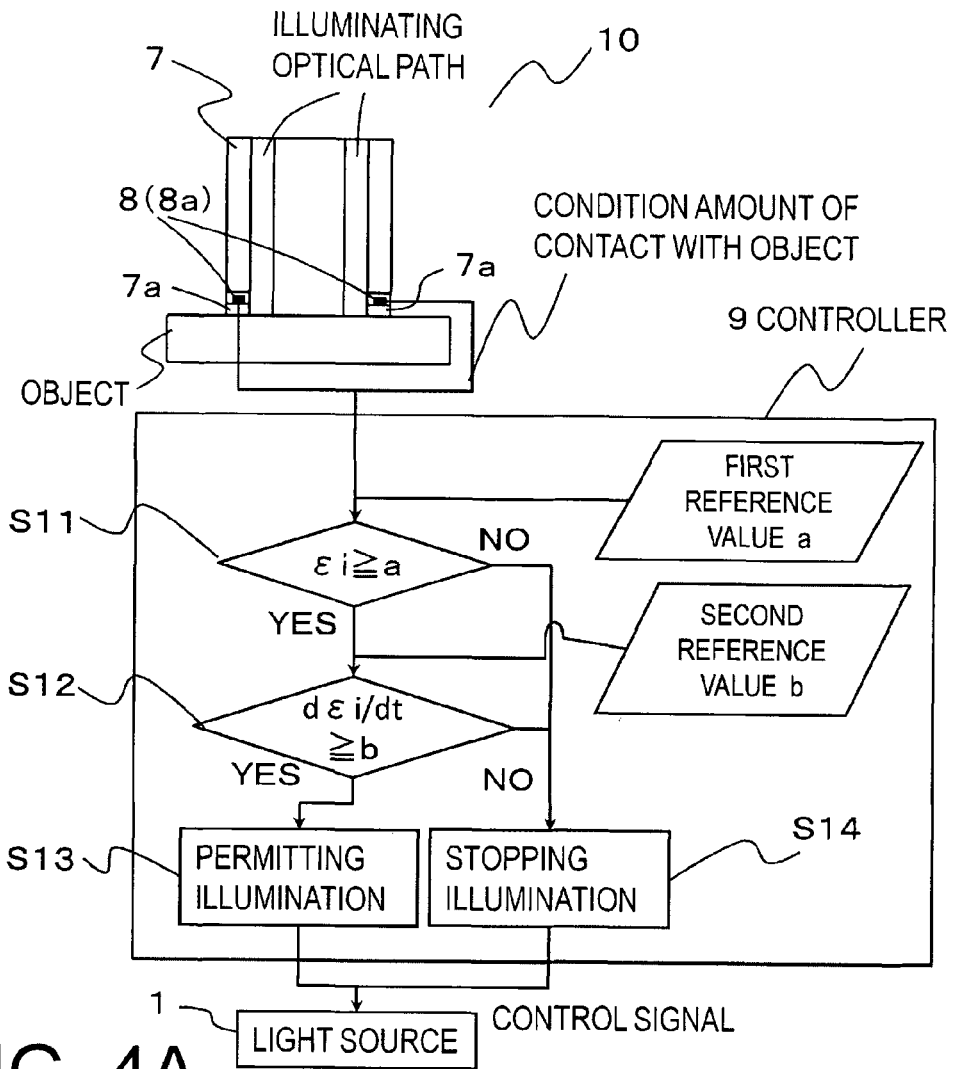
FIGS. 4A and 4B are diagrams illustrating a light illumination control method according to embodiment 1 of the present invention.

In Embodiment 1, the control method carried out by the controller 9 is described more specifically with reference to FIG. 4A. The controller 9 carries out the following process to control emission of illuminating light based on the condition amount of contact with the object inputted from the touch sensor 8.

The controller 9 determines whether or not the contact condition is equal to or more than the predetermined first reference value (step S11). In cases where the strain gauge 8a is used as the touch sensor 8, if the strain amount $\epsilon i \geq a$ (first reference value), the process proceeds to the subsequent step S12. If $\epsilon i < a$, the process proceeds to step S14. In these expressions, i represents the channel number of the strain gauge 8a (i.e., touch sensor 8).

The controller 9 determines whether or not the change in contact condition is equal to or more than the predetermined second reference value (step S12). More specifically, the controller 9 determines whether or not the temporal differential of the contact condition is equal to or more than the second reference value. In cases where the strain gauge 8a is used as the touch sensor 8, if $d\epsilon i/dt \geq b$, the process proceeds to the subsequent step S13. If $d\epsilon i/dt < b$, the process proceeds to step S14. The change in contact condition which occurs in pressing the handheld probe 10 against the object is expressed as a positive value, while that occurs in separating the handheld probe 10 from the object is expressed as a negative value. The second reference value b is a negative value.

The controller 9 controls the light source 1 to permit illumination (step S13). Alternatively, the controller 9 may control a non-illustrated shutter or both of the light source and the shutter.

The controller 9 controls the light source 1 to stop illumination (step S14). Alternatively, the controller 9 may control the non-illustrated shutter or both of the light source and the shutter.

Step S11 and step S12 may be replaced with each other.

Figure 4B:
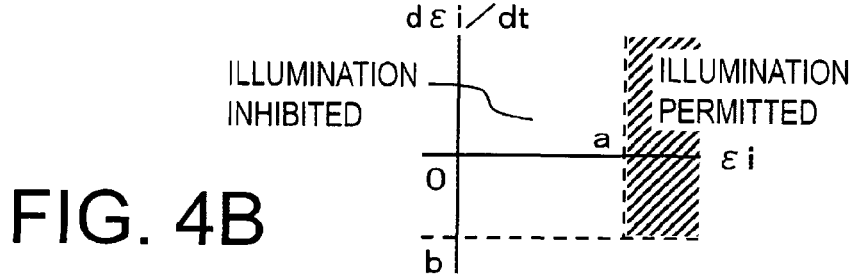

According to the control method of the present embodiment, the control is performed such that illumination is permitted when each of the contact condition amount (horizontal axis: strain amount $\epsilon i$) and the change thereof (vertical axis: $d\epsilon i/dt$) in FIG. 4B falls within an illumination permitted region (hatched region) while illumination is stopped when the contact condition amount and the change thereof fall within an illumination inhibited region. In one example using the strain gauge 8a mounted on the flat spring 7a as in Embodiment 1, control was performed under the conditions : the first reference value a=0.05; and the second reference value b=−0.1. As a result, the handheld probe 10 and the object were brought into intimate contact with each other without leaning against each other on one side. There is no limitation to these values, but the values have to be varied to meet the conditions including the material of the flat spring 7a, the shape and size of the flat spring 7a, and the elasticity modulus of the object.

In the foregoing description, the amount of the change in contact condition which occurs in pressing the handheld probe 10 against the object is expressed as a positive value, while that occurs in separating the handheld probe 10 from the object is expressed as a negative value, and the second reference value b is a negative value. However, the reverses of the plus, minus and inequality signs are effective. In steps S11 and S12, the expressions: $\epsilon i \geq a$; and $d\epsilon i/dt \geq b$ as the conditions to be satisfied have equality signs. However, the expressions: $\epsilon i > a$; and $d\epsilon i/dt > b$ without the equality signs are also effective. It is possible to find the moving average value of the condition amount of contact (strain amount $\epsilon i$) with the object and then use the moving average value for the determinations in steps S11 and S12. This holds true for the following Embodiments.

The amount of change in contact condition has been described as the temporal differential of the contact condition amount. The sampling time Δt is set arbitrarily. For example, the sampling time maybe a sampling frequency (about 1 kHz) with which the output of the touch sensor 8 is inputted to the controller 9 or may be about several seconds for which sampling is performed to determine a difference to be used as the amount of change in contact condition.

According to the present embodiment, the illumination control signal can be quickly transmitted to the light source 1 before the handheld probe 10 is separated from the object even when the sensors for detection of contact are disposed in such a manner as not to circumscribe the illuminating area. Therefore, the safety against laser irradiation can be secured without the need to provide a multiplicity of such sensors. Further, the number of sensors for detection of contact can be reduced and, hence, the housing 7 can be downsized. As a result, the handheld probe 10 can be wholly downsized.

While the foregoing description has been made of the photoacoustic apparatus as an example, the subject to which the present invention is applicable is not limited to such a photoacoustic apparatus. The present invention is applicable to other object information acquiring apparatuses including an AOT (Acousto-Optical Tomography) apparatus and a DOT (Diffuse Optical Tomography) apparatus. Further, the present invention is applicable to light irradiation control for laser therapy apparatuses without limitation to such object information acquiring apparatuses. That is, the present invention can be said to be applicable to any light irradiating apparatus including a handheld probe with a light irradiating mechanism.

Embodiment 2

In the control method described in Embodiment 1, the first reference value a of the contact condition amount (strain amount $\epsilon i$) and the second reference value b of the change in the contact condition amount (temporal differential of the strain amount $d\epsilon i/dt$) are predetermined values. These values may be varied to meet the contact condition.

In Embodiment 2, the reference value of the contact condition amount (i.e., first reference value) is varied in accordance with the change in the contact condition amount. This is because the contact condition amount between the handheld probe 10 and the object varies due to a difference in intimate contact condition between the operation of pressing the handheld probe 10 against the object and the operation of separating the handheld probe 10 from the object. For example, a force of not less than 8 N is needed to bring the handheld probe 10 and the object into intimate contact with each other in the operation of pressing the handheld probe 10 against the object, whereas a force of about 3 N is needed to bring the handheld probe 10 and the object into intimate contact with each other in the operation of separating the handheld probe 10 from the object. For this reason, the first reference value of the contact condition amount (strain amount $\epsilon i$) is determined in accordance with the temporal differential of the contact condition ($d\epsilon i/dt$).

In a method for the determination of the first reference value, an expression is stored in the controller 9 for determining the first reference value as a function of the temporal differential of the contact condition. Alternatively, a table may be stored in the controller 9 for determining the reference value of the contact condition amount in accordance with the temporal differential of the contact condition. Yet alternatively, it is possible that with the first reference value being two-valued, whether the handheld probe 10 has to be pressed against the object or separated from the object is determined from the temporal differential of the contact condition, followed by selection of a reference value of the contact condition amount based on the determination thus made.

Figure 5A:
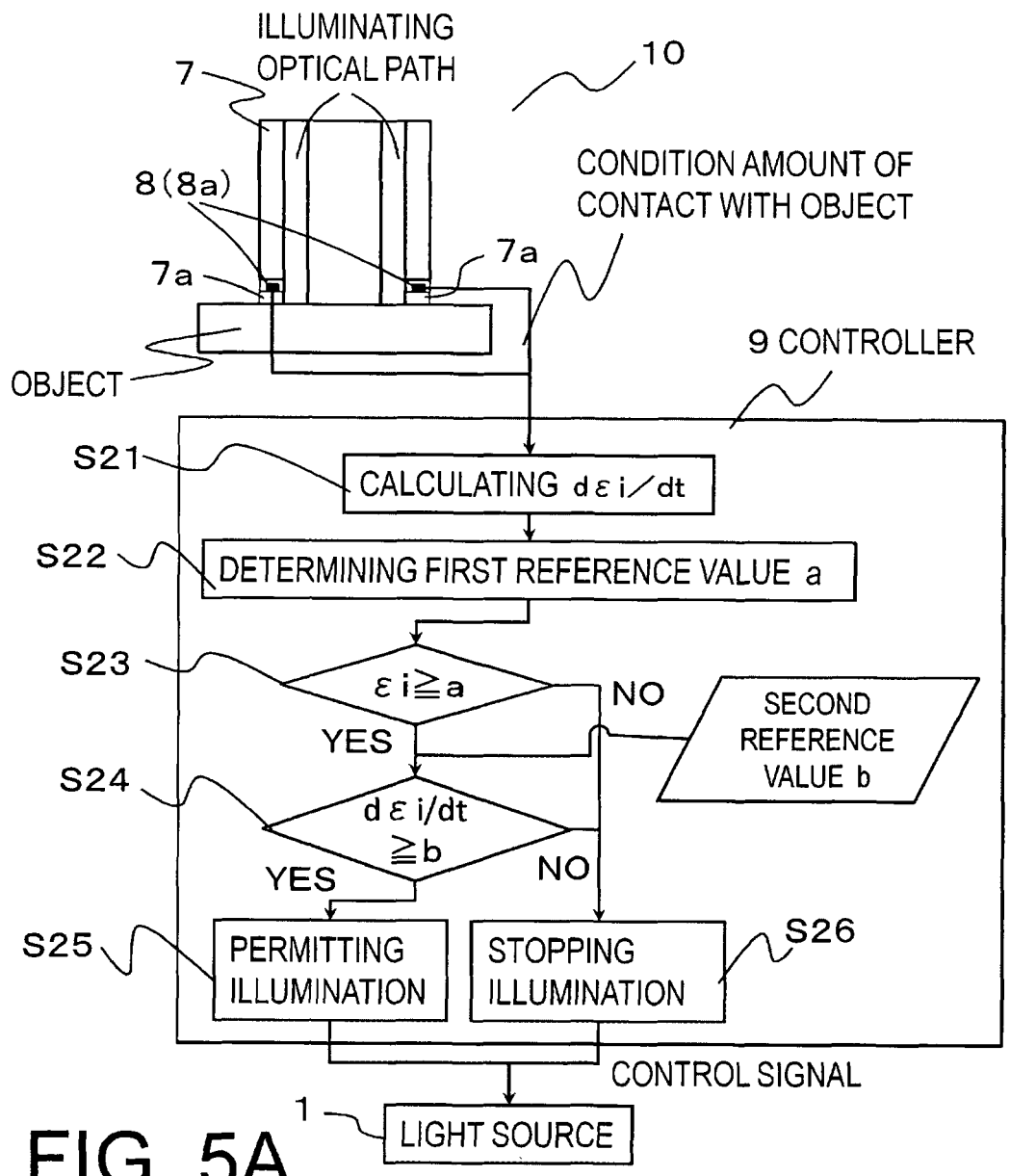
FIGS. 5A and 5B are diagrams illustrating a light illumination control method according to embodiment 2 of the present invention.

As shown in FIG. 5A, the controller 9 carries out the following process to control emission of illuminating light based on the contact condition amount between the touch sensor 8 and the object.

The controller 9 calculates the change in contact condition (step S21). In cases where the strain gauge 8*a* is used as the touch sensor 8, the controller 9 calculates $d\epsilon i/dt$. In the expression, i represents the channel number of the strain gauge 8*a* (i.e., touch sensor 8).

The controller 9 determines the first reference value of the contact condition amount (step S22). In cases where the strain gauge 8*a* is used as the touch sensor 8, the controller 9 determines the reference value a of the strain amount.

The controller 9 determines whether or not the contact condition is equal to or more than the first reference value determined in step S22 (step S23). In cases where the strain gauge 8*a* is used as the touch sensor 8, if $\epsilon i \geq a$ (reference value), the process proceeds to the subsequent step S24. If $\epsilon i < a$, the process proceeds to step S26.

The controller 9 determines whether or not the change in contact condition is equal to or more than the predetermined second reference value (step S24). More specifically, the controller 9 determines whether or not the temporal differential of the contact condition is equal to or more than the second reference value b. In cases where the strain gauge 8*a* is used as the touch sensor 8, if $d\epsilon i/dt \geq b$, the process proceeds to the subsequent step S25. If $d\epsilon i/dt < b$, the process proceeds to step S26. The change in contact condition which occurs in pressing the handheld probe 10 against the object is expressed as a positive value, while that occurs in separating the handheld probe 10 from the object is expressed as a negative value. The second reference value b is a negative value.

The controller 9 controls the light source 1 to permit illumination (step S25). Alternatively, the controller 9 may control a non-illustrated shutter or both of the light source and the shutter.

The controller 9 controls the light source 1 to stop illumination (step S26). Alternatively, the controller 9 may control the non-illustrated shutter or both of the light source and the shutter.

Step S23 and step S24 maybe replaced with each other.

Figure 5B:
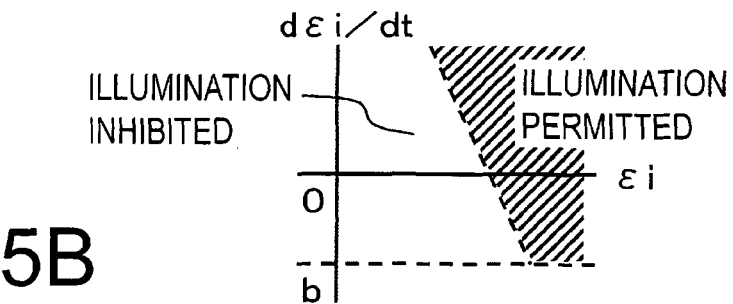

According to the control method of the present embodiment, the first reference value a used in pressing the handheld probe 10 against the object is set to a low value as shown in FIG. 5B. On the contrary, the first reference value a used in separating the handheld probe 10 from the object is set to a high value. By so doing, illumination is permitted even when the intimate contact between the handheld probe 10 and the object is weak in pressing the handheld probe 10 against the object. For this reason, there is no need to exert a force more than necessary on the object in pressing the handheld probe 10 against the object, which leads to improvement in the operability of the apparatus.

Embodiment 3

In Embodiment 3, the second reference value is determined from the contact condition amount. This is because the intimate contact condition between the handheld probe 10 and the object differs according to the condition in which the handheld probe 10 is pressed against the object. For example, after the handheld probe 10 has been pressed against the object with a relatively strong force, the pressing force is relieved while maintaining the intimate contact. Even when this operation causes a large change in the contact condition amount to occur in the direction away from object, the intimate contact can be maintained. Therefore, the second reference value b of the change in contact condition ($d\epsilon i/dt$) is determined in accordance with the contact condition amount (strain amount $\epsilon i$). In a method for the determination of the second reference value b, an expression is stored in the controller 9 for determining the second reference value b as a function of the contact condition amount. Alternatively, a table may be stored in the controller 9 for determining the reference value of the change in contact condition in accordance with the contact condition amount.

Figure 6A:
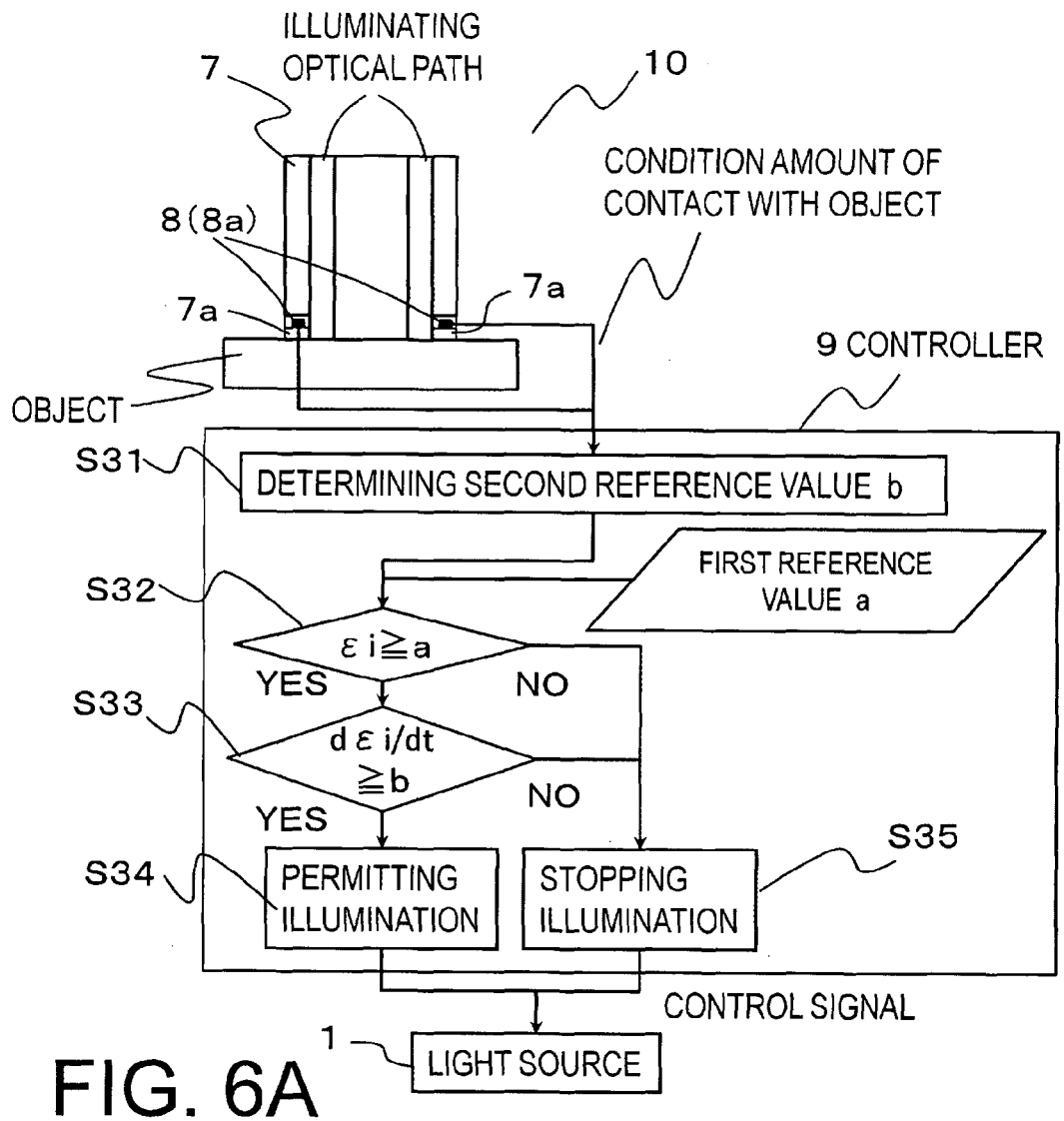
FIGS. 6A and 6B are diagrams illustrating a light illumination control method according to embodiment 3 of the present invention.
Figure 6B:
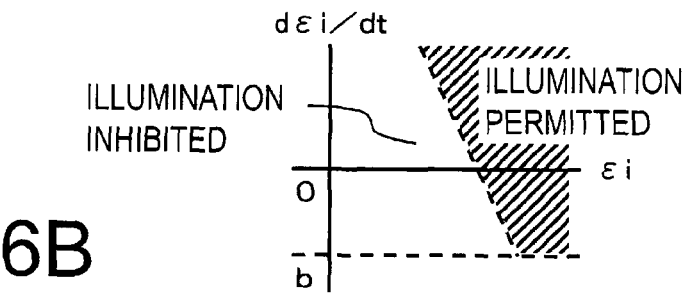
Figure 7A:
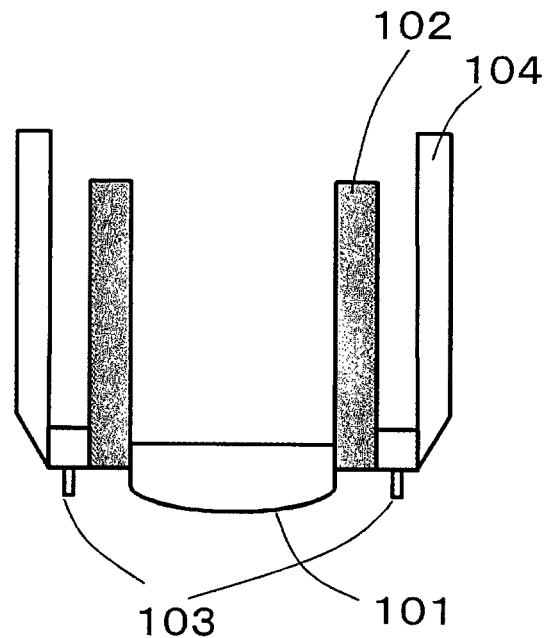
FIGS. 7A and 7B are views illustrating the background art.
Figure 7B:
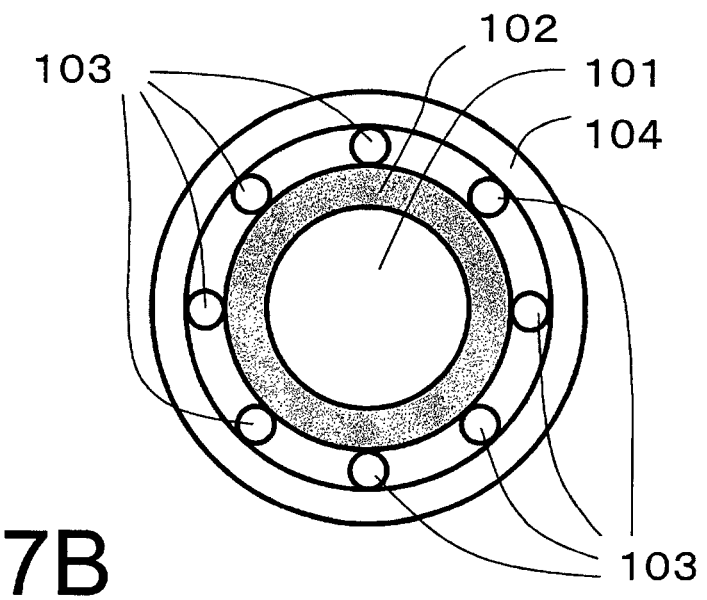

As shown in FIG. 6A, the controller 9 carries out the following process to control emission of illuminating light based on the contact condition amount between the touch sensor 8 and the object.

The controller 9 determines the second reference value from the contact condition amount (step S31). In cases where the strain gauge 8*a* is used as the touch sensor 8, the controller 9 determines the second reference value b for determination of the change in strain amount (the temporal differential).

The controller 9 determines whether or not the contact condition is equal to or more than the predetermined first reference value (step S32). In cases where the strain gauge 8*a* is used as the touch sensor 8, if the strain amount $\epsilon i \geq a$ (reference value), the process proceeds to the subsequent step S33. If $\epsilon i < a$, the process proceeds to step S35. In these expressions, i represents the channel number of the gauge 8*a* (i.e., touch sensor 8).

The controller 9 determines whether or not the change in contact condition is equal to or more than the second reference value determined in step S31 (step S33). More specifically, the controller 9 determines whether or not the temporal differential of the contact condition is equal to or more than the predetermined second reference value b. In cases where the strain gauge 8*a* is used as the touch sensor 8, if $d\epsilon i/dt \geq b$, the process proceeds to the subsequent step S34. If $d\epsilon i/dt < b$, the process proceeds to step S35. The change in contact condition which occurs in pressing the handheld probe 10 against the object is expressed as a positive value, while that occurs in separating the handheld probe 10 from the object is expressed as a negative value. The second reference value b is a negative value.

The controller 9 controls the light source 1 to permit illumination (step S34). Alternatively, the controller 9 may control a non-illustrated shutter or both of the light source and the shutter.

The controller 9 controls the light source 1 to stop illumination (step S35). Alternatively, the controller 9 may control the non-illustrated shutter or both of the light source and the shutter.

Step S32 and step S33 may be replaced with each other.

According to the control method of the present embodiment, when the handheld probe 10 is strongly brought into intimate contact with the object, the second reference value b is set to a relatively low value to permit illumination even when the change in contact condition becomes large in the direction away from the object. On the contrary, when the handheld probe 10 is weakly brought into intimate contact with the object, the second reference value b is set to a relatively high value based on which whether or not to illuminate is determined. By so doing, illumination is permitted even when the intimate contact between the handheld probe 10 and the object is somewhat relieved in pressing the handheld probe 10 against the object strongly, but unless the change in contact condition is in the pressing direction to reach the intimate contact, illumination is inhibited when the intimate contact is weak. This feature can suppress, for example, the occurrence of an inconvenience such that laser light emission is undesirably stopped even when the pressing force is relieved with the intimate contact maintained after the handheld probe 10 has been pressed against the object with a relatively strong force. For this reason, the operability of the apparatus is further improved.

Embodiments 2 and 3 may be combined with each other in such a manner that the reference value of the contact condition amount and the reference value of the change in the direction away from the object are each determined in accordance with the contact condition amount measured by the touch sensor 8.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An object information acquiring apparatus comprising:
a probe including an irradiating unit which guides light from a light source to an object, a housing containing the irradiating unit, an ultrasound probe configured for acquiring an acoustic wave that is generated in response to the object being irradiated with light from said irradiating unit, and a touch sensor configured for acquiring a contact condition amount between the object and the housing; and
a controller comprising a CPU configured for controlling irradiation with light from the irradiating unit based on a level of the contact condition amount and a change in the contact condition amount per unit time,
wherein, in a case in which the contact condition amount is equal to or more than a first reference value and the change in the contact condition amount per unit time is equal to or more than a second reference value, the controller performs a control which enables irradiation with light from the irradiating unit, and
in a case in which the contact condition amount is less than the first reference value or the change in the contact condition amount per unit time is less than the second reference value, the controller performs a control which disables irradiation with light from the irradiating unit, based on the assumption that the change in the contact condition amount which occurs when the housing is pressed against the object is positive,
wherein the first reference value is varied according to the change in the contact condition amount.

2. The object information acquiring apparatus according to claim 1, wherein the change in the contact condition amount is a time derivative of the contact condition amount.

3. The object information acquiring apparatus according to claim 1, wherein said controller is configured to perform the control by decreasing the first reference value as a value of the change in the contact condition amount is increased.

4. The object information acquiring apparatus according to claim 1, wherein said touch sensor is a strain gauge disposed on said housing, and the contact condition amount is a strain amount of said housing.

5. The object information acquiring apparatus according to claim 1, further comprising a processor configured for creating image information about an internal part of the object from the acoustic wave.

6. A method for controlling an object information acquiring apparatus having a probe including an irradiating unit which guides light from a light source to an object, a housing containing the irradiating unit, an ultrasound probe configured for acquiring an acoustic wave that is generated in response to the object being irradiated with light from said irradiating unit, and a touch sensor configured for acquiring a contact condition amount between the object and the housing, and a controller configured for controlling irradiation with light from the irradiating unit, the method comprising:
a step of causing the controller to determine whether or not a change in the contact condition amount per unit time is equal to or more than a second reference value and the contact condition amount is equal to or more than a first reference value, based on the assumption that the change in the contact condition amount which occurs when the housing is pressed against the object is positive; and
a step of causing the controller to perform a control which enables irradiation with light from the irradiating unit in a case in which the contact condition amount is equal to or more than the first reference value and the change in the contact condition amount per unit time is determined to be equal to or more than the second reference value, and
in a case in which the contact condition amount is less than the first reference value or the change in the contact condition amount per unit time is less than the second reference value, causing the controller to perform a control which disables irradiation with light from the irradiating unit,
wherein the first reference value is varied according to the change in the contact condition amount.

* * * * *